(12) United States Patent
Long et al.

(10) Patent No.: US 6,520,035 B2
(45) Date of Patent: Feb. 18, 2003

(54) CONTROL SYSTEM FOR BELT SAMPLE CUTTERS

(75) Inventors: John B. Long, Knoxville, TN (US); Armistead M. Long, Austin, TX (US)

(73) Assignee: Heron Holdings, Knoxville, TN (US)

( * ) Notice: Subject to any disclaimer, the term of this patent is extended or adjusted under 35 U.S.C. 154(b) by 32 days.

(21) Appl. No.: 09/935,309

(22) Filed: Aug. 22, 2001

(65) Prior Publication Data

US 2002/0000131 A1 Jan. 3, 2002

Related U.S. Application Data

(63) Continuation of application No. 09/272,519, filed on Mar. 19, 1999, now abandoned.

(51) Int. Cl.[7] .............................. G01N 1/12; G01N 1/00; G01N 1/20; B01L 3/00
(52) U.S. Cl. .................. 73/864.32; 73/863; 73/863.56; 73/864.91
(58) Field of Search .............................. 73/863, 863.56, 73/863.81, 864.32, 864.41, 864.91

(56) References Cited

U.S. PATENT DOCUMENTS

| | | | | |
|---|---|---|---|---|
| 3,998,090 A | * | 12/1976 | Wislocki | 73/12 |
| 4,409,853 A | * | 10/1983 | Chase et al. | 73/863 |
| 4,562,747 A | * | 1/1986 | Jaeger | 73/863.54 |
| 4,619,149 A | | 10/1986 | Long | |
| 4,884,462 A | * | 12/1989 | Long | 73/863.91 |
| 4,919,000 A | | 4/1990 | Long | |
| 5,385,058 A | * | 1/1995 | Krauss | 73/864.32 |
| 5,505,096 A | | 4/1996 | Long | |
| 5,604,996 A | * | 2/1997 | Bestwick et al. | 34/484 |
| 5,767,421 A | | 6/1998 | Long et al. | |

* cited by examiner

Primary Examiner—Hezron Williams
Assistant Examiner—Katina Wilson
(74) Attorney, Agent, or Firm—Luedeka, Neely & Graham P.C.

(57) ABSTRACT

An apparatus is provided for extracting cross-sectional samples of bulk material from a moving belt conveyor with a rotating sample cutter. The sample cutter is driven around a circular sampling path by a pair of double-acting pneumatic cylinders that are connected to angularly offset crank throws. Fluid flow in and out of each pneumatic cylinder pressure chamber is independently regulated as a function of the respective cylinder rod position and direction of movement whereby both chambers may be simultaneously open to the pressure supply or to the atmospheric vent for a brief rotational arc.

13 Claims, 5 Drawing Sheets

US 6,520,035 B2

CONTROL SYSTEM FOR BELT SAMPLE CUTTERS

This case is a continuation of application Ser. No. 09/272,519, filed Mar. 19, 1999, now abandoned.

BACKGROUND OF THE INVENTION

The present invention relates to bulk material sampling systems and more particularly, to systems for extracting samples of bulk material from a moving conveyor belt.

Bulk material such as particulate coal or ore that is transported in a continuous stream by a belt conveyor is often the subject of cross-stream sampling. The usual objective of such cross-stream sampling is the characterization of certain material properties for the purposes of quality and value determination. The quality and character of a material sample frequently determines the value or use of that material deposited along the belt within a reasonable proximity of the sample. Consequently the statistical accuracy of sample representation is extremely important.

One example of equipment for extracting a material sample from the moving surface of a belt conveyor comprises a rotating sample cutter that is positioned to be driven about a rotational path that crosses the conveyor belt path. As the cutter transversely engages the material stream carried by the moving belt, that segment of material in the belt stream located between the rotational planes of the cutter side walls is swept or scooped into the cutter bin and becomes the sample increment.

As a general principle, the more rapidly the cutter passes through the material flow stream, the more accurate and reliable is the sample representation. The specification of U.S. Pat. No. 5,767,421, the disclosure of which is hereby incorporated by reference, describes the mechanics of how a rapidly moving cutter extracts a more complete and valuable representation of the material carried by the belt.

An independent incentive for greater cutter speed is the mathematical interrelationship between the width of the cutter opening, the material particle size and the belt speed. This interrelationship is described with respect to FIGS. 1A through 1C and is predicated on an empirical principle of statistical sampling that the effective cutter opening width, i.e. measured parallel with the belt traveling direction, should be between 2.5 to 3 times the width of the largest particle in the loose agglomeration of material particles that are the subject of the sample. FIG. 1A represents an increment of particulate material 10 deposited in an elongated pile on a stationary carrier belt 12. The material extraction swath 14a is that width of material removed from the elongated pile by passage of the cutter through the pile. The rotational planes 16a and 16b respective to the cutter sidewalls define the maximum width dimension of the swath 14a. If the width of swath 14a is 3 times greater than the effective diameter of the largest particle in the material pile 10 when the belt is stationary as represented by FIG. 1A, the normal width of swath 14b is reduced to 2.57 times the particle diameter when the cutter, moving at 1000 ft/min, traverses a belt 12 moving at 600 ft/min as illustrated by FIG. 1B. The normal motion vectors define a resultant angle of 59° between the cutter side planes 16a and 16b and the belt traveling direction. This 59° resultant angle reduces the normal width of the swath 14b to only 2.57 times the particle diameter.

FIG. 1C shows that for the same cutter moving at a speed of 700 ft/min traversing the belt moving at 1000 ft/min, the resultant vector angle is 35° and the normal swath width 14c is only 1.72 times the particle size: an unacceptably low ratio.

Larger rotary belt samplers are usually driven by a pair of double-acting pneumatic cylinders. The cutter structure is secured for 360° rotation about an axis or axle shaft. The axle shaft passes through two bearing supports. The cutter rotates in a swath between the supports. Outside of the cutter rotational swath, usually on opposite sides of the cutter swath, are a pair of crank throws radiating from the cutter axle shaft. The crank throws are structurally rigid with the axle shaft and cutter and angularly offset about the axle shaft axis whereby one rotatively leads the other about the axle shaft axis by about 20° to 50°; usually about 40°. Each of these crank throws is pivotally connected to the rod end of a respective double-acting, single rod cylinder. The bore end of the cylinder unit usually is pivotally secured to a stationary axis aligned substantially parallel with the cutter rotational axis.

Characteristic of a double-acting cylinder is the use of pressurized fluid, i.e. air, on both sides of a piston that is structurally secured to a rod. Consequently, the cylinder has two pressure chambers. In those machines having the rod projecting from only one side of the piston, i.e. a single rod cylinder, these two chambers may be further distinguished as the head chamber and the rod chamber. This distinction is significant due to respectively different working areas and volumes. The working area and volume of the rod chamber is less than that of the head chamber by the area and volume of the rod that is stroked by displacement of the piston along the cylinder bore. The operative result of these distinctions is that greater fluid pressure is required in the rod chamber than the head chamber to produce the same rod force. However, more fluid volume is required in the head chamber than the rod chamber to produce the same rod displacement distance. Due to the many characteristics of a compressible fluid that effect the mass, density and flow rate across an orifice or through a port aperture, the optimum valve timing for opening and closing fluid flow ports respective to the head and rod chambers of a double acting cylinder is different.

Valve timing is generally referenced to the physical position of the piston within the cylinder bore when fluid is admitted to or released from a chamber. For example, when the rod is extended from the cylinder to the maximum, the piston position may be characterized as the upper dead center position. The opposite extreme, when the rod is drawn into the cylinder to the maximum degree, is characterized as the lower dead center position. Intermediate positions are characterized as before or after a center (upper or lower) position. If the outer end of the rod is connected to a crank throw, such intermediate positions may be designated in terms of crank rotational degrees.

Traditionally, fluid flow respective to the two chambers of a double-acting cylinder that drives a crank throw about a full 360° rotation is controlled by a single "4-way valve". The "4-way" reference is to the number of conduit connection ports in the valve body. Two ports are dedicated to the fluid flow respective to the two pressure chambers in the cylinder. One valve port is dedicated to the fluid pressure supply and the fourth valve port is dedicated to the spent fluid discharge e.g. atmosphere. Operation of the valve "spool" connects the pressure supply alternately with the rod chamber and the head chamber. Simultaneously, when the rod chamber is connected with the fluid supply, the head chamber is connected with the fluid discharge. No relative timing in the sequence of these four events is possible. The usual prior art practice, for example, is to switch the 4-way valve spool when the piston reaches upper dead center and switch again when the piston reaches lower dead center.

The consequence of an invariant prior art valve sequence is exacerbated by the structural fact that all working fluid must pass through the same 4-way valve twice in a rod stroke cycle. In effect, the fluid flow port of each chamber is as long as the respective conduit that connects the 4-way valve. The volume of each chamber is increased accordingly. Hence, when the valve spool shifts, pressurized fluid must first negate the inertia of the out flowing fluid to begin the fluid inflow. Sufficient fluid must thereafter enter the chamber flow port conduit to raise the pressure along the conduit before any force is transferred to the piston face. Simultaneously, when the valve spool opens a conduit to atmosphere, the pressure in the conduit, when opened, is at a maximum. Hence, the high pressure air in the conduit must be released before the pressure force on the piston face opposing opposite piston and rod movement is reduced.

Each of these transitional events require time and a discreet portion of the operational cycle. Moreover, because of the rod area/volume differential in a double-acting, single rod cylinder, the times required for charging and venting respective to the two chambers of a cylinder are not identical. Hence, twice in each rod cycle, the force flow from the rod declines thereby resulting in the rotational speed reduction of a belt sample cutter.

It is, therefore, an object of the present invention to optimize the valve timing for cutter drive cylinders.

Another object of the invention is a means to increase the rotational speed of a belt sample cutter: preferably without a supply pressure increase.

Also an object of the invention is a more efficient breathing system for double-acting pneumatic cylinders.

An additional object of the invention is provision for independent timing control over the respective pressure chambers of a double-acting cylinder.

A further object of the invention is the provision of minimum length fluid flow conduits respective to the pressure chambers of a double-acting cylinder.

Another object of the invention is a means to abruptly stop rotation of a sample cutter at a predetermined position around the cutter rotational circle.

Another object of the invention is a means to selectively reverse rotate the cutter to a predetermined park position around the cutter rotational circle and secure the cutter at the park position indefinitely.

SUMMARY OF THE INVENTION

Another object of the invention is a means to selectively reverse rotate the cutter to a predetermined park position around the cutter rotational circle and secure the cutter at the park position indefinitely.

These and other objects of the invention as will emerge from the following detailed description of the preferred embodiments are achieved by providing the double acting, single rod drive cylinders for a rotary sample cutter with closely coupled, 3-way valves that, preferably are solenoid actuated. Such a 3-way valve or the equivalent is connected in close proximity to each of the opposite pressure chambers in a single cylinder. The common port of each 3-way valve is connected, preferably by a close nipple, to the fluid flow port respective to a single pressure chamber. The discharge port of each 3-way valve is preferably open directly to atmosphere through a minimum length of conduit. The pressure supply port of one 3-way valve respective to one pressure chamber may be connected in parallel with that of the other 3-way valve respective to the other pressure chamber in the same cylinder.

The timing of each valve is individually triggered by a corresponding proximity switch that engages a solenoid to open and close the 3-way valve for one pressure chamber to pressure supply without regard to the status of pressure supply to the other pressure chamber.

Accordingly, the pressure supply may be opened to a pressure chamber while the piston is still approaching the upper dead center position. Also, the opposite, expanding pressure chamber may be opened to atmosphere prior to the piston lower dead center position. However, the two changes in fluid flow control need not occur simultaneously since the volume differential between the head chamber and the rod chamber will occasion different mass flow rates and inertia.

In brief, both chambers may be simultaneously pressurized or vented to atmosphere at operator discretion. Hence, the drive cylinders may be operated in a cutter braking mode as well as a rotational drive mode. Moreover, the rotary sample cutter may be rotationally reversed, selectively positioned and positionally held.

BRIEF DESCRIPTION OF THE DRAWINGS

The preferred embodiments of my invention will hereafter be described in detailed reference to the drawings wherein.

DESCRIPTION OF THE PREFERRED EMBODIMENTS

Figure 1A:
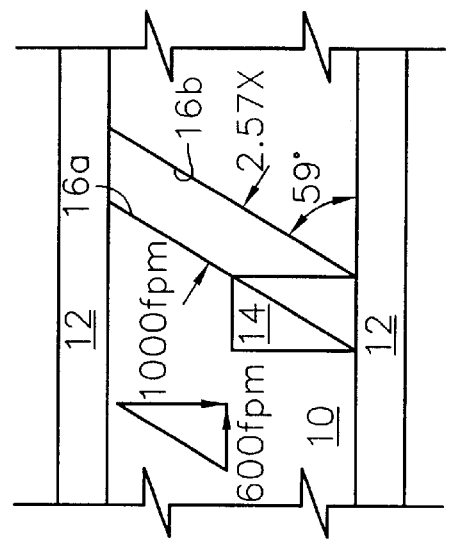
FIGS. 1A through 1C schematically illustrate the relationships between the speed of a sample cutter, the speed of the conveyor belt and the width of the sample swath extracted by the cutter.
Figure 1B:
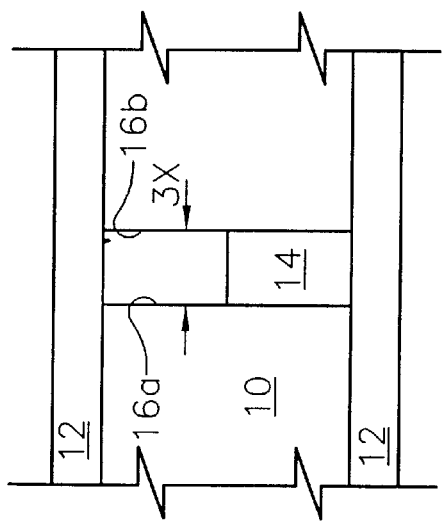
Figure 1C:
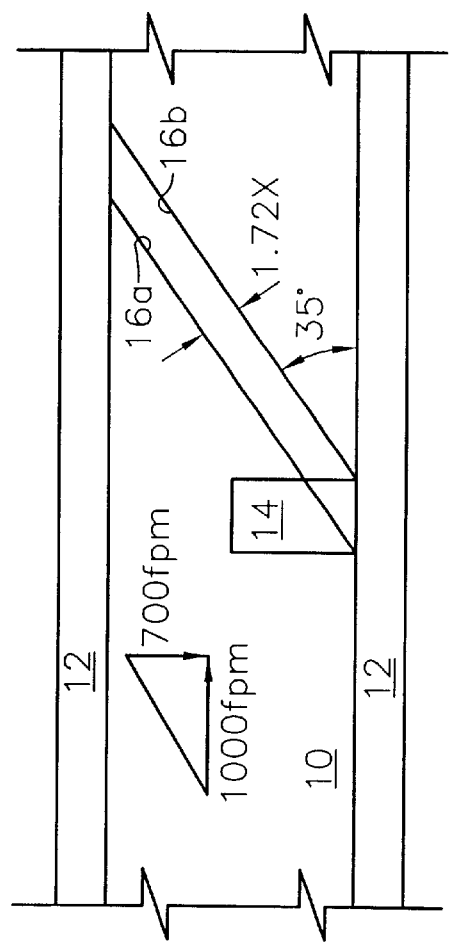
Figure 2:
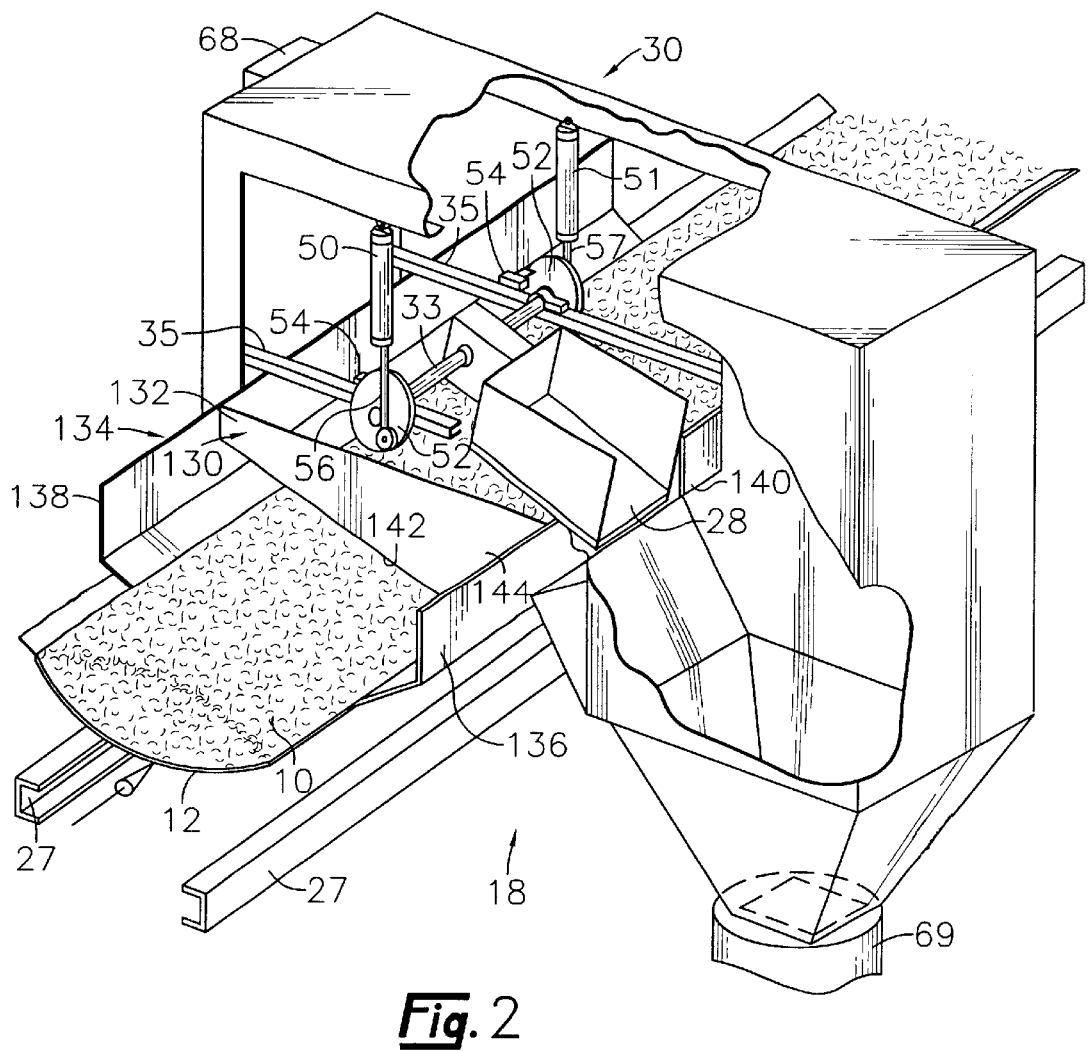
FIG. 2 is a perspective view of a belt conveyor and a rotary sampling system with cutaway portions.

Referring now to the drawings wherein like reference characters designate like or similar elements throughout the several figures of the drawings, FIG. 2 illustrates a typical conveyor belt sampling system 18 to which the invention applies. Such a sampling system includes a continuous belt conveyor 12 supported upon a plurality of idlers for transporting a stream of bulk particulate material 10 along the belt length. The belt sampling system 18 includes a cutter 28 mounted for rotation about an axis above the belt 12. The cutter 28 is thus supported in position for removing a cross-stream increment of particulate material 10 from the belt as the cutter is rotated about its axis. Suitable collection means, such as chute 69, is positioned to one side of the belt 12 for receiving the bulk material increment that is removed from the belt 12 by the cutter 28.

An increment-collecting cycle may be concluded by parking the cutter 28 adjacent the chute side of the belt 12 so that the opening of the chute 69 is covered by the cutter 28 in a manner that prevents untimely or undesired egress of bulk material from the belt 12. The cutter may be maintained in this parked positioned until a subsequent increment collection cycle is initiated.

The belt 12 is appropriately supported by transverse idlers in a trough-like configuration. The belt 12 is driven by any suitable means as, for example, a drive motor, located adjacent an end of the belt 12.

With reference still to FIG. 2, the cutter 28 is rotatable relative to the frame structure 30 in a plane substantially perpendicular to the direction of the belt 12 movement. Frame structure 30 includes a base which, in the depicted system 18, is secured to the fixed-frame structure 27 of the belt conveyor. Cutter 28 is preferably fixedly attached to a shaft 33 which is rotatably mounted on transversely-extending support members 35 extending across opposite sides of the frame structure 30 and spaced apart longitudinally of the direction of movement of the belt 12. Thus, the shaft 33 is supported above and aligned parallel to the line of movement of the belt 12.

In order to effect rotation of the shaft 33 and the sampler 28, the opposite ends of the shaft 33 are appropriately connected to double-acting pneumatic cylinders 50 and 51 through discs 52 provided on the shaft ends. The distal ends of the piston rods 56 and 57 respective to cylinders 50 and 51 are pivotally secured to respective discs 52 at a point radially removed from the axis of the shaft 33. Consequently the discs 52 serve as crank throws for translating the linear movement of the cylinders 50 and 51 into rotation of the shaft 33 and cutter 28. Moreover, the crank throw radii are angularly separated about the shaft 33 axis by about 20° to about 50°, preferably about 40°. By introducing pressurized air into the cylinders 50 and 51 in a sequential manner to thereby move the piston rods 56 and 57 respective to the cylinders 50 and 51 between extended and retracted conditions, the cylinders 50 and 51 force the shaft 33 and thus the cutter 28 to rotate at a very high speed across the belt to extract a representative sample of material 10 from the fast moving belt 12. The cutter 28 is moved under power from the cylinders 50 and 51 throughout its pass across the belt 12.

Figure 3:
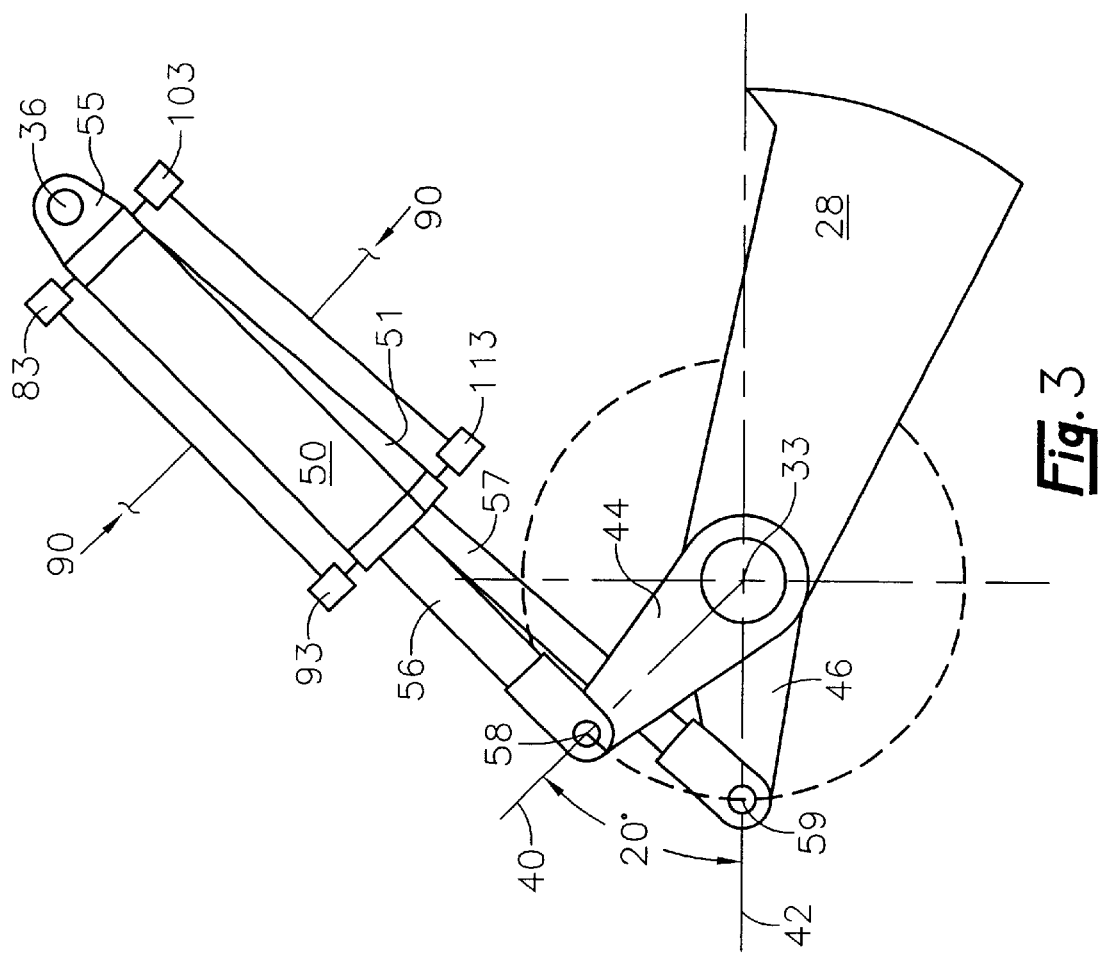
FIG. 3 is a side view of a sample cutter drive assembly.

The angular separation between crank throw radii about the axis of the axle shaft 33 is emphasized by the FIG. 3 embodiment wherein the crank throw radii 40 and 42 are structurally defined by crank arms 44 and 46. Each of these crank arms 44 and 46 is non-rotatively secured to the axle shaft 33 on laterally opposite sides of the sample cutter 28. The piston rods 56 and 57 respective to the cylinders 50 and 51 are pivotally secured to the crank arms 44 and 46 by clevis links and pivot pins 58 and 59. The crank throw radius 40 intersects the axle shaft 33 axis and the axis of pivot pin 58. Crank throw axis 42 intersects the axle shaft 33 axis and the axis of pivot pin 59. The angular separation between the crank throw radii 40 and 42 about the axis of axle shaft 33 is represented by the arc 20.

Braking of the cutter 28 may be accomplished by appropriate control of the flow of air into the cylinders 50 and 51 so that the cutter 28 may be abruptly stopped at a preselected position thereby ejecting a sample increment into the collection chute 69. Similarly, the cutter may be reverse rotated to and/or parked at a preselected position. Supplemental friction braking means 54 may be mounted with and appropriately connected to the cylinders 50, 51 for fail-safe operation in case of a loss of air pressure. For example, the braking means 54 may be spring-operated and air released and includes pneumatically-actuated calipers for acting against the surfaces of the discs 52 to hold the cutter 28 in a raised position so that it cannot slip down and interfere with the material flow.

Control means are mounted on the frame structure 30 of the sampling apparatus for systematic operation of the system 18. More particularly, the control means selectively actuates the cylinders 50 and 51 to impart a rotational force on the cutter 28 causing the latter to rotate with the shaft 33 for segregation and extraction of a cross-stream increment of bulk material from the belt 12 and then return the cutter 28 to the park position and actuate braking means 54 to hold the cutter 28 in the park position after removal of the cross-stream increment. Preferably, the control means 68 includes a control computer which is preset in accordance with predetermined timing or location as to sample taking, free of selection on a discretionary basis by an operator, and is operative so that the systematic and sequential operation thereof is performed within a relative short period of time.

The system 18 may also include means for limiting the buildup of bulk material against the upstream side surface of the cutter 28 as the cutter is moved through the bulk material 10. In the illustrated system 18, the limiting means includes a surge dam 130 in the form of a plate 132 positioned immediately adjacent to and upstream of the cutter 28, and oriented generally perpendicular to the flow path of the bulk material 10. The dam 130 is supported at each end by a skirt arrangement 134 which is, in turn, appropriately mounted to the underlying belt supporting structure 27 in a manner that maintains the skirt arrangement 134 in a fixed position relative to the structure 27. The skirt arrangement 134 includes side skirts 136, 138 extending along a section of the belt length. These side skirts 136, 138 are preferably constructed in such manner as to not appreciably retard the flow of material along the belt 12, even though the lower edges of the skirts 136, 138 may overlap the edges of the belt 12 and contact the edges of the load profile as illustrated in FIG. 2. One skirt 136, as best shown in FIG. 2, defines an opening or cutout 140 adjacent the frame structure 30 which accommodates passage of the cutter 28 therethrough during an increment-collecting cycle for subsequent ejection of the collected increment into the chute 69. During operation of the belt 12, the skirt arrangement 134 reduces any likelihood of spillage of the bulk material from the belt 12 in the vicinity of the frame 30 between increment-collecting cycles or during sampler stall.

The plate 132 of the surge dam also includes an upstream-projected face 144 having a lower edge 142 which is positioned to span the upper surface of the bulk material 10 and extend angularly downwardly from side skirt 138. As bulk material builds up by a predetermined amount against the upstream side of the cutter 28 and to the right of the belt vertical midplane, the surge dam 130 intercepts the additional buildup and its lower edge grades the bulk material buildup toward one side, or the left side as viewed in FIG. 2 of the belt 12.

Figure 4:
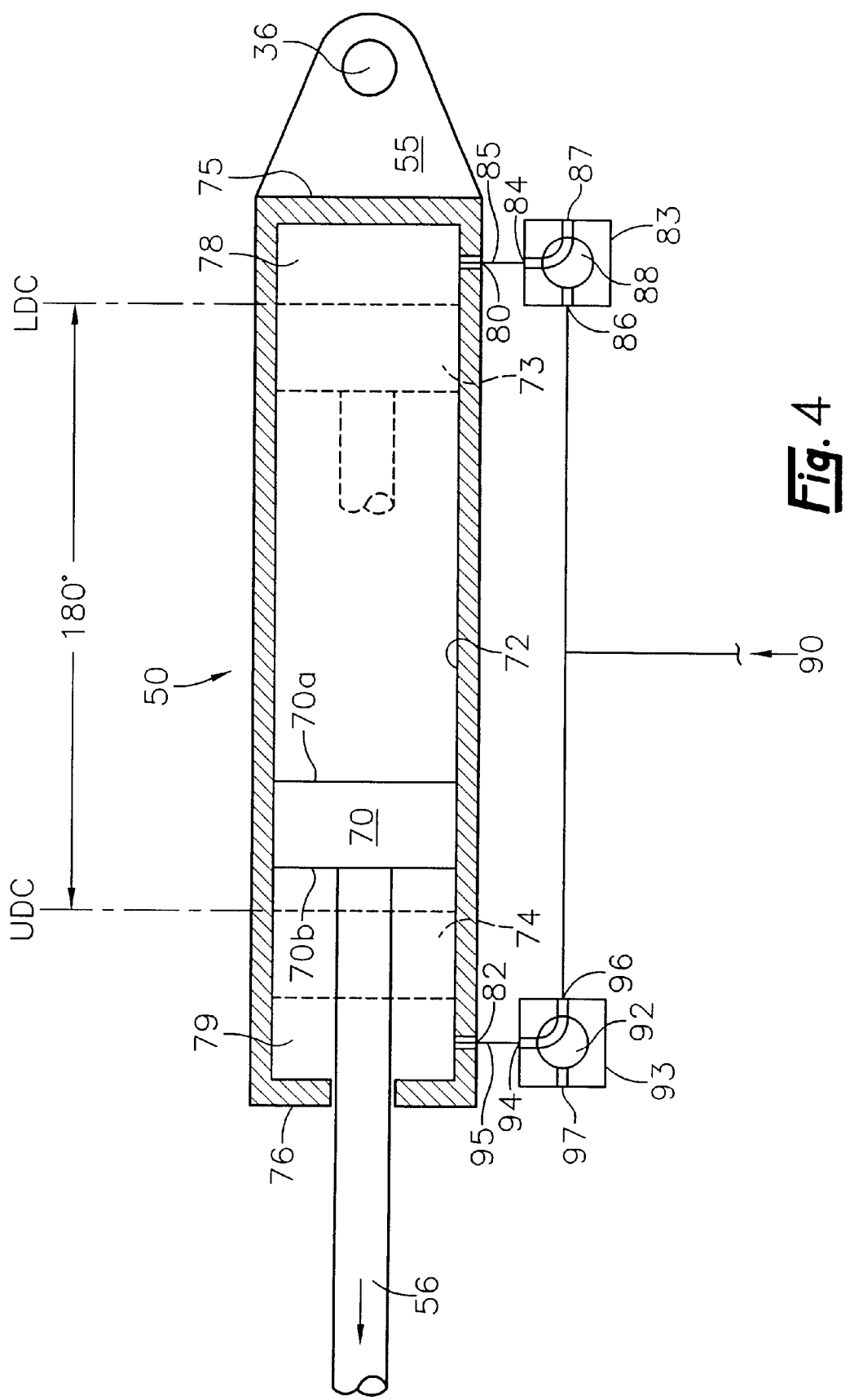
FIG. 4 is a cross-section of a cutter drive cylinder.

Referring again to FIG. 3, the double-acting pneumatic cylinders 50 and 51 usually are single rod cylinders whereby a piston rod 56 and 57 extends from only one face of a two-faced internal piston. With respect to the FIG. 4 partial cross-section of cylinder 50, the internal piston 70 reciprocates along the cylinder bore 72 between stroke extremes 73 and 74 respective to the head end 75 and rod end 76 of the cylinder. Both cylinder units 50 and 51 are pivotally secured to the frame structure 30 by bearing housings 55 about a common rocker axis 36, for example.

That variable volume within the cylinder bore 72 between the cylinder head 75 and the proximate piston face 70a is generally characterized as the head chamber 78. The variable volume between the rod end 76 of the cylinder and the proximate piston face 70b is generally characterized as the rod chamber 79. Working fluid such as compressed air is transferred in and out of the head chamber 78 through one or more head ports 80. One or more rod ports 82 serve the rod chamber 79.

In a preferred embodiment of the invention, fluid flow through each of these ports 80 and 82 of double-acting pneumatic cylinder 50 is controlled by a respective 3-way valve 83 and 93. Double-acting pneumatic cylinder 51 has corresponding 3-way valves 103 and 113. As used herein, the term "3-way valve" refers to a fluid flow control device having two conduit connection ports that are alternatively connected to a common connection port. In the present example, the common port 84 for the 3-way valve 83 is connected by a "close" or very short nipple 85 to the head chamber port 80. One selectively connected port 87 is open diretly to the atmosphere. The other selectively connected port 86 is connected to a standing air pressure supply 90. A rotatable control element 88 usually described as a "spool," selectively switches the common port connection 84 with either the atmosphere port 87 or the pressure port 86 by a 90° oscillation. Such 90° oscillation of a rotary spool 88 or reciprocation of a slide spool not shown may be driven mechanically by an adjustable linkage from the rod 56 or by a solenoid controlled by a proximity switch that is adjustably positioned relative to the rod or piston.

Fluid flow in and out of the rod chamber 79 is controlled by the 3-way valve 93 having a common valve port 94 connected to the rod port 82 by a close nipple 95. Rotary spool 92 alternatively connects the common port 94 with the pressure port 96 or the vent port 97. Oscillation of the rotary spool 92 is usually by the same type mechanism as drives the spool 88 for the head chamber valve 83. flowever, the exact moment of each valve function is set independently of the other.

Valve timing for double acting single rod cylinders is usually set in reference to the rod or piston position. With respect to FIG. 4, lower dead center (LDC) position is shown to be the position 73 of piston 70 where the piston face 70a is most proximate to the cylinder head 75. Upper dead center (UDC) position is at piston position 74 where the piston face 70b is most proximate to the cylinder rod end 76. The piston stroke is the linear distance between these two extreme piston positions. Related to the sample cutter 28, the piston stroke is two times the radial length of the crank arms 44 and 46. The crank throw radius 40 coaxially aligns twice with the rod reciprocation axis in a 360° revolution of the cutter shaft 33. When the rod clevis pin 58 is most proximate to the cylinder 50, the rod 56 is drawn within the cylinder bore 72 to the maximum degree. This is the lower dead center (LDC) position. Conversely, when the clevis pin 58 is most remote from the cylinder 50, the rod 56 is withdrawn from the cylinder bore 72 to the maximum degree. This is the upper dead center (UDC) position.

In a traditional 4-way valve control, valve spool timing is usually set to the UDC and LDC positions. When the piston reaches each of the UDC and LDC positions the valve spool switches. Since the single gating spool of the 4-way valve simultaneously controls the fluid flow direction in both cylinder chambers, no accommodation may be made for the inertia and compressibility of the working fluid or of the volumetric differential between the head chamber and the rod chamber.

The present invention frees the interdependence of the head and rod chambers whereby the head port 80 may be opened to the pressure supply 90 by a few degrees of crank 44 rotation prior to LDC. Simultaneously, the rod port 82 may continue connection with the pressure supply 90 until the piston 70 reaches LDC. Consequently, the control valves 83 and 93 may be timed for a valve lap whereby both chambers are opened to the pressure supply simultaneously for a few degrees of crank 44 rotation.

Figure 5:
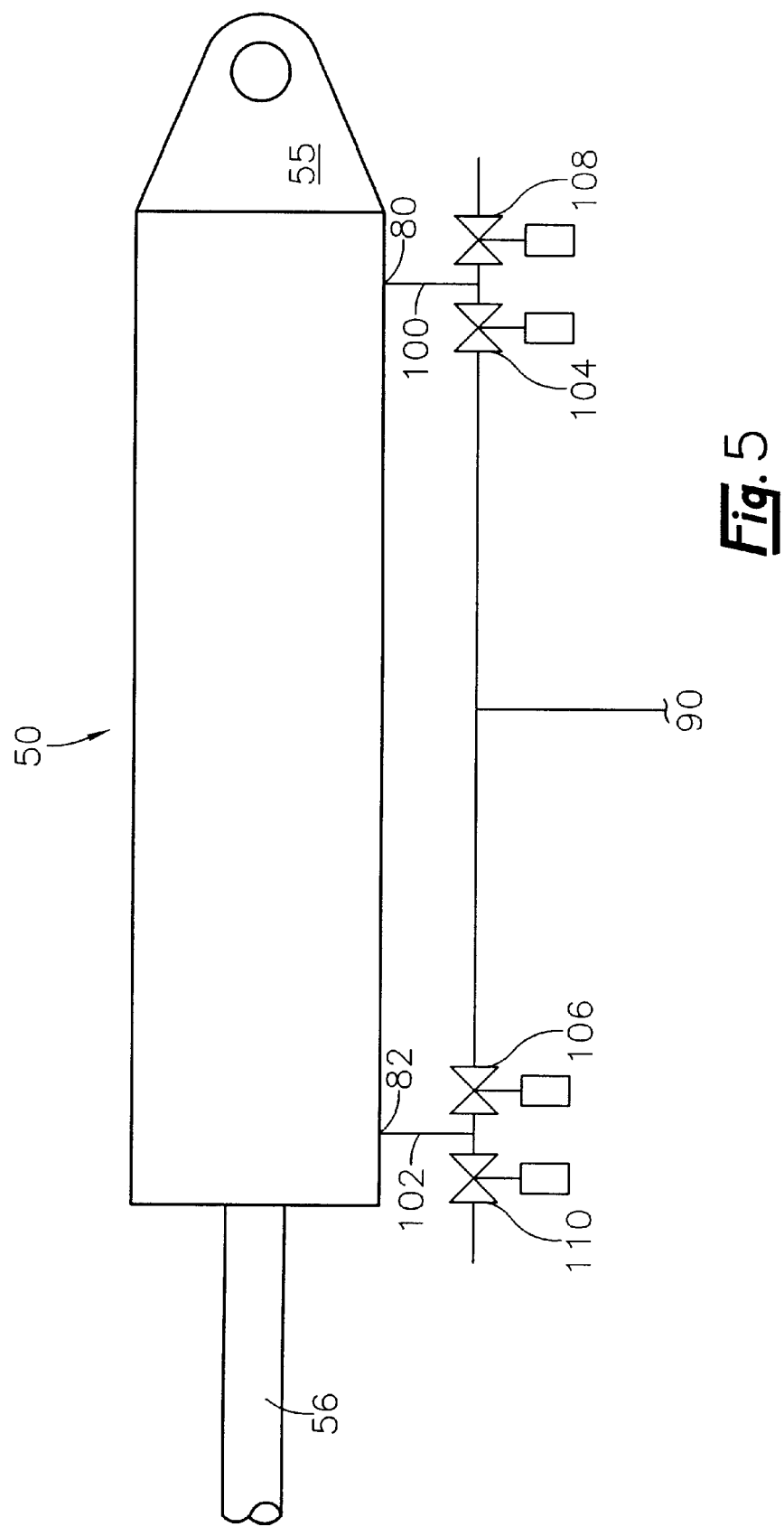
FIG. 5 is a schematic of an alternative fluid control embodiment for the cutter drive cylinders.

FIG. 5 illustrates an embodiment of the invention having even greater flexibility for chamber flow control. In this embodiment, the head and rod chamber ports 80 and 82 are connected to tee joints 100 and 102. Single acting, normally closed solenoid valves 104 and 106 control the passage of pressure fluid from the source 90 into the respective tee joints. Independently, single acting, normally closed solenoid valves 108 and 110 control the opening of the tee joints to an atmospheric vent. By this embodiment, a cylinder chamber may be selectively closed to both the pressure source 90 and the vent for the purpose of either braking movement of the cutter 28 or holding it at the park position.

The foregoing description of preferred embodiments for the invention has been presented for purposes of illustration and description. It is not intended to be exhaustive or to limit the invention to the precise forms described herein. Obvious modifications or variations are possible in light of the above teachings. The embodiments were chosen and described to provide the best illustrations of the invention principles and its practical application to thereby enable one of ordinary skill in the art to utilize the invention in various embodiments and with various modifications as is suited to the particular use contemplated. All such modifications and variations are within the scope of the invention as determined by the appended claims when interpreted in accordance with breadth to which they are fairly, legally, and equitably entitled.

Having fully described the preferred embodiments of my invention, those of ordinary skill in the art will understand the prior art mechanics and equivalents of implementation. As my invention, therefore,

We claim:

1. A system for extracting a sample of bulk particulate material solids carried on an elongate conveyor belt which is supported, at least adjacent the system, in an arcuate cross-sectional configuration, said system comprising:

a sample cutter mounted for rotation about a rotational axis aligned above and substantially parallel with the conveyor belt for removing a cross-sectional increment sample of the material carried on said conveyor belt by movement of the sample cutter across the belt through the material along an arcuate path adjacent the surface of the belt, said sample cutter being rotatively driven about said rotational axis by at least a pair of double-acting fluid cylinders that are each pivotally secured to respective crank throws at pivot axes that are displaced radially from said rotational axis, said crank throws being structurally secured to said sample cutter and angularly displaced about said rotational axis from each other, said fluid cylinders having a pair of pressure chambers for reciprocally displacing a cylinder rod in at least one direction to various positions, each of said pressure chambers respective to each cylinder having separate valve means for regulating a flow of pressurized fluid into and from the respective chamber, said valve means having respective operator means for coordinating the flow direction of fluid for the respective chamber independently of fluid flow directions determined for other chambers among fluid cylinders driving said sample cutter such that each pressure chamber may pressurized or vented independently of any pressurization or venting of the other pressure chamber.

2. A system as described by claim 1, wherein fluid flow respective to each chamber is regulated by three-way valve means having three fluid flow ports, a first of said flow ports in close coupled connection with the respective chamber, a second flow port in close coupled connection with ambient atmosphere and a third flow port connected with a pressurized fluid supply source.

3. A system as described by claim 2, wherein said first flow port is alternately connected with said second and third flow ports by alternate positions of a single valve spool element.

4. A system as described by claim 3, wherein positionment of said valve spool element is regulated by the displacement direction and position of the cylinder rod.

5. A system as described by claim 3, wherein alternate positions of said spool element are set by solenoid operator means.

6. A system as described by claim 2, wherein said second and third flow ports are respectively opened and closed by solenoid operated valves.

7. A system as described by claim 6, wherein the solenoid operated valves respective to said second flow ports are opened and closed independently of opening and closing of the solenoid operated valves respective to said third flow ports.

8. A system for extracting a sample of bulk particulate material solids carried on an upper surface of an elongate moving conveyor belt to provide a representative sample of solids carried on the belt for analysis, the belt being supported, at least adjacent the system, in an arcuate cross-sectional configuration by at least one set of garland idler rollers, said set having two or more spaced-apart idler rollers supported beneath the belt adjacent a sampling location in a substantially overall arcuate configuration;

a sample-cutter pivotally mounted on a sampler frame adjacent the sampling location for pivotal movement about an axis aligned above and substantially parallel with a movement direction of the conveyor belt at the sampling location for removing a cross-sectional increment sample of the material carried on the upper surface of the belt by rapidly moving the sample-cutter transversely across the belt through the material along an arcuate path adjacent the upper surface of the belt, said arcuate path being sufficiently long to cause the sample-cutter to pass substantially completely across the belt, and said sample-cutter being pivotally driven about said axis along said arcuate path by at least one double-acting fluid cylinder pivotally connected to said sample-cutter and to said sampler frame, said fluid cylinder having first and second pressure chambers for reciprocally displacing a cylinder rod therein to various positions to rotatably move the sample-cutter about the axis along the arcuate path and through the material on the belt, said cylinder being operatively connected to first and second valves for independently regulating flow of pressurized fluid into and from the respective first and second pressure chambers in said cylinder, said vlaves being operable to coordinate the flow direction of fluid into and out of respective chambers of said cylinder with respect to a position of the sample-cutter along said actuate path.

9. The system of claim 8, wherein said arcuate path extends 360 degrees about the axis during rotatable movement of the sample-cutter therealong.

10. The system of claim 8, further comprising a second fluid cylinder pivotably connected to said sampler frame and having a third pressure chamber for reciprocally displacing a cylinder rod therein operably connected to said sample-cutter for causing movement of said sample-cutter with respect to material carried on the belt, said second fluid cylinder being operatively connected to a third valve for regulating flow of pressurized fluid into and from said third pressure chamber with respect to the position of the sample-cutter in said system in relation to material carried on the belt.

11. The system of claim 8, wherein the axis is a substantially fixed distance above the modulated belt.

12. The system of claim 10, wherein the cylinder in conjuction with the second cylinder is operable to move the sample-cutter along a second arcuate path to a ready or parked position after completion of sample taking, wherein the second arcuate path is a greater distance from the belt than the arcuate path traversed by the sample-cutter during sample taking.

13. The system of claim 12, wherein the second arcuate path is a continuation of the arcuate path and provides 360 degrees rotation of the sample-cutter about the axis.

* * * * *